United States Patent
Menzler et al.

(10) Patent No.: US 7,264,943 B2
(45) Date of Patent: Sep. 4, 2007

(54) METHOD FOR PRODUCING CEPHALEXIN

(75) Inventors: Stefan Menzler, Darmstadt (DE);
Thomas Boller, Darmstadt (DE);
Hans-Ulrich Petereit, Darmstadt (DE);
Christian Meier, Darmstadt (DE)

(73) Assignee: Roehm GmbH & Co. KG, Darmstadt (DE)

( * ) Notice: Subject to any disclaimer, the term of this patent is extended or adjusted under 35 U.S.C. 154(b) by 482 days.

(21) Appl. No.: 10/501,140

(22) PCT Filed: Oct. 16, 2003

(86) PCT No.: PCT/EP03/11480

§ 371 (c)(1),
(2), (4) Date: Jul. 13, 2004

(87) PCT Pub. No.: WO2004/050893

PCT Pub. Date: Jun. 17, 2004

(65) Prior Publication Data

US 2005/0084925 A1 Apr. 21, 2005

(30) Foreign Application Priority Data

Dec. 3, 2002 (DE) ................ 102 56 656

(51) Int. Cl.
*C07D 501/22* (2006.01)
*C12P 35/04* (2006.01)

(52) U.S. Cl. ........................ 435/47; 540/230

(58) Field of Classification Search ............ None
See application file for complete search history.

(56) References Cited

U.S. PATENT DOCUMENTS

| 4,582,860 A | 4/1986 | Bigwood et al. |
| 6,060,268 A * | 5/2000 | De Vroom .................. 435/45 |
| 7,011,963 B1 * | 3/2006 | Meier et al. ................. 435/180 |

FOREIGN PATENT DOCUMENTS

| DE | 19804518 | 8/1999 |
| WO | 97/04086 | 2/1997 |

OTHER PUBLICATIONS

Travascio et al., Biotechnology and Bioengineering vol. 79, Issue 3, pp. 334-346 (Aug. 2002).*
Travascio et al., Biotechnol. Prog., 18 (5), 975-985, (Jul. 2002).*
L. Cao et al., Journal of Molecular Catalysis B: Enzymatic, vol. 11, Issues 4-6, Jan. 22, 2001, pp. 665-670.*
Janssen Michiel H A et al: "Evaluation of the performance of immobilized penicillin G acylase using active-site titration" Biotechnology and Bioengineering, Bd. 78, Nr. 4, May 20, 2002, pp. 425-432, XP002274659 & ISSN: 0006-3592, the whole document.

* cited by examiner

*Primary Examiner*—Mark L. Berch
(74) *Attorney, Agent, or Firm*—Oblon, Spivak, McClelland, Maier & Neustadt, P.C.

(57) ABSTRACT

The invention relates to a process for the preparation of cephalexin with the aid of a penicillin amidase immobilized on a crosslinked hydrophilic copolymer which has binding activity for ligands having nucleophilic groups and is in bead form.

15 Claims, No Drawings

METHOD FOR PRODUCING CEPHALEXIN

The invention relates to a process for the preparation of cephalexin with the aid of a penicillin amidase immobilized on a crosslinked hydrophilic copolymer which has binding activity for ligands having nucleophilic groups and is in bead form.

PRIOR ART

Processes for the synthesis of semisynthetic beta-lactam antibiotics by acylation of a beta-lactam residue (beta-lactam nucleus) with an activated side chain, such as, for example, an amide or an ester, using enzyme penicillin acylase (penicillin amidase) are well known to the skilled worker.

In most of these cases, the enzyme if bound to a solid, water-insoluble carrier and is subsequently brought into contact in aqueous solution with the beta-lactam nucleus and the activated side chain.

The disadvantage of the processes disclosed to date is the fact that the ratio of the synthesis of the desired compound by the enzyme compared with the hydrolysis of the activated side chain to worthless side chain acids and also to the hydrolysis of the desired product, the so-called S/H value, is often unfavorable and makes economic production difficult.

WO 93/12250 discloses that in the synthesis of the semisynthetic beta-lactam antibiotics cephadroxil and cephalexin by *E. coli* penicillin amidase immobilized on Eupergit® (Röhm GmbH & Co. KG, Darmstadt, Germany, see also comparative example 1) the SOH value can be beneficially influenced by the choice of the reaction conditions. An influence of the nature of the carrier material is, on the other hand, not disclosed. The particular disadvantage of the process disclosed in WO 93/12250 is that the cephalexin is isolated from the reaction mixture in a complex with beta-naphthol, so that subsequent purification steps are necessary, and product losses occur.

Attempts have therefore been made to develop optimized carrier materials. Thus, WO 97/04086 discloses an *E. coli* penicillin amidase which is immobilized on a carrier material composed of a swelling agent and a polymer having free amino groups, and the use thereof for preparing beta-lactam derivatives. The disclosed process for preparing cephalexin has, however, the disadvantage that the beta-lactam nucleus 7-aminodeacetoxycephalosporanic acid (7-ADCA) is employed in a three-fold molar excess compared with the activated side chain D-phenylglycinamide (PGA). If the above-stoichiometry amounts of beta-lactam nucleus are employed, the nucleus must be recycled on the industrial scale in order to be able to operate economically. This is costly and leads to losses of yield. In addition, this circumstance also leads to impurities in the product because the nucleus is unstable.

EP 0 730 035 likewise discloses the preparation of cephalexin on a specific carrier in acceptable yields. However, the particle size of the carrier material used (Emphaze™) is only 60-80 μm. This is a great disadvantage for industrial applications. Thus, chromatography columns packed with such material have only a low flow rate.

A carrier material for enzymes is described in DE 198 04 518. It is mentioned that the material can be used for enzymatic synthesis of amoxycillin and ampicillin. Suitability for synthesizing cephalexin using immobilized penicillin amidase is not mentioned.

Problem and Solution

In view of the prior art discussed above, the present invention was therefore based on the problem of providing an improved process for the synthesis of cephalexin which overcomes the above-mentioned disadvantages.

This process was particularly intended to make it possible to achieve a favorable S/H value. It was further intended that the particle size of the carrier material used be from 120 to 250 μm, which is favorable for industrial processes.

This problem is solved by the process defined in claim 1. Preferred embodiments of the process of the invention are defined in the dependent claims which refer back to claim 1.

In particular, it is possible in a technically simple manner which could not have been predicted to solve the above problem by crosslinked hydrophilic carrier polymer materials which have binding activity for ligands having nucleophilic groups, are in bead form and can be prepared by inverse bead polymerization of a monomer phase which consist of monomers and a diluent, where the monomers present are (a) 5-40% by weight of hydrophilic monomers which are capable of free-radical polymerization, have a vinyl group and form at least 10% strength aqueous solutions at room temperature, (b) 30-50% by weight of monomers which are capable of free-radical polymerization and have a vinyl group and an additional functional group which is able to enter into covalent bonds in a polymer-analogous reaction with the nucleophilic groups of the ligands, (c) 20-60% by weight of crosslinking monomers which are capable of free-radical polymerization and have two or more ethylenically unsaturated polymerizable groups, with the proviso that a), b) and c) add up to 100% by weight, and the diluent used is a mixture of methanol and water in the ratio from 1:1.0 to 1:4.0, where the monomer phase is dispersed to droplets in a continuous phase composed of an organic solvent composed of an aliphatic hydrocarbon having 5-7 carbon atoms, where the ratio of monomer phase to continuous phase is from 1:2.0 to 1:4.0, and in this form undergo free-radical polymerization in the presence of a polymerization initiator and of a protective colloid, with the proviso that the ratio of the monomers to the diluent is from 1:1.7 to 1:2.4, being coated with penicillin amidase, and these coated carriers being brought into contact with an aqueous solution which comprises (i) 7-aminodeacetoxycephalosporanic acid and
(ii) D-phenylglycinamide.

in ratios of from 1:2 to 2:1, preferably 1.5:1 to 1:1.5, particularly preferably in approximately equal molar ratios, i.e. in ratios of from 1.2:1 to 1:1.2.

The carrier material used and the process for its preparation are described in DE 198 04 518.

Implementation of the Invention

Preparation of the Carrier Material

Monomers

In order to ensure the hydrophilicity of the monomer mixture, it must consist predominantly of hydrophilic monomers. By hydrophilic monomers are meant those monomers which form at least 10% strength aqueous solutions at room temperature and preferably comprise no ionic group or groups which can be ionized by addition of acid or base.

Monomers a) are 5-40, 8-35, in particular 9-12, % by weight of hydrophilic monomers which are capable of free-radical polymerization and have a vinyl group which form at least 10% strength aqueous solutions at room temperature.

Particularly suitable monomers a) are acrylamide and/or methacrylamide, with preference for methacrylamide. Further examples are hydroxyalkyl esters of unsaturated polymerizable carboxylic acids, such as hydroxyethyl acrylate and hydroxyethyl methacrylate or N-vinylpyrrolidone.

Monomers b) are 30-50, preferably 35-45, % by weight of monomers which are capable of free-radical polymerization and have a vinyl group and an additional functional group, preferably an oxirane group (epoxy group), which is able to enter into covalent bonds in a polymer-analogous reaction with the nucleophilic groups of the ligands. Oxirane groups in particular are suitable for binding ligands with retention of their biological activity.

Preferred monomers b) are glycidyl methacrylate and/or allyl glycidyl ether. It is particularly preferred for both monomers to be employed simultaneously in approximately equal amounts.

Monomers c) are 20-60, in particular 25-55, particularly preferably 40-55, % by weight of hydrophilic, crosslinking monomers which are capable of free-radical polymerization and have two or more ethylenically unsaturated polymerizable groups. Preferred monomers c) are N,N'-methylenebisacrylamide or N,N'-methylenebismethacrylamide. N,N'-methylenebismethacrylamide is particularly preferred. It is also possible where appropriate to employ 0-10% by weight of further crosslinking monomers which are capable of free-radical polymerization and have two or more ethylenically unsaturated polymerizable groups. Hydrophilic di(meth)acrylates are suitable, such as, for example, polyethylene oxide di(meth)acrylates.

Monomers a), b) and c) in each case add up to 100% by weight.

Diluents

The monomer phase consists of monomers a) to c) dissolved in a diluent which must be a mixture of methanol and water in the ratio from 1:1.0 to 1:4.0. Particularly favorable mixing ratios for methanol and water are from 1:1.2 to 1:2.5, in particular from 1:1.3 to 1:1.7.

Ratio of Monomers to Diluent

The ratio of monomers to diluent is particularly critical. This must be in the range from 1:1.7 to 1:2.4, particularly preferably in the range from 1.9 to 2.1.

Continuous Phase

A suitable continuous phase is an organic solvent which is an aliphatic hydrocarbon having 4 to 7 C atoms. n-heptane is preferred, and cyclohexane is particularly preferred.

Monomer Phase/Continuous Phase Ratio

The ratio of the monomer phase to a continuous phase formed by the organic solvent must be from 1:2.0 to 1:4.0, preferably between 1:2.8 to 1:3.3.

Further Process Conditions

As further constituents, the suspended monomer phase comprises in a manner known per se polymerization initiators, with preference for sulfur-free initiators, and with particular preference for 4,4'-azobis(4-valeric acid), and protective colloids (emulsifiers) such as, for example a copolymer with 95 parts of n-butyl methacrylate and 5 parts of 2-trimethylammoniumethyl methacrylate chloride having weight average molecular weights in the range from 30 000 to 80 000.

The bead polymerization (also referred to as suspension polymerization) is otherwise carried out in a known manner by, for example, introducing the continuous phase and the protective colloid, and dispersing the monomer phase, in which the initiator is also present, with stirring, e.g. at 40 to 60° C., in the organic phase, and subsequently heating to 60-70° C. The water/methanol mixture can be removed azeotropically almost completely for example over a period of 6 hours. The mixture is allowed to react to the end for about 3-5 hours and is subsequently cooled to room temperature. The resulting beads are filtered off with suction and dried for example in vacuo for 12 hours. An alternative possibility is also for the bead polymers to be filtered off and washed with water. Drying is preferably carried out in a fluidized bed dryer, because solvent residues can be removed particularly efficiently in this way. The resulting polymer beads (=carrier polymer material) have a size in the range from 50 to 500 µm, in particular from 120 to 250 µm. By the binding capacity is meant the enzymatic activity which can be reached on maximum loading of the carrier polymer material with a particular enzyme. The binding capacity is expressed as penicillin amidase activity in units per g of carrier polymer beads [U/g moist]. The binding capacity of the carrier polymer beads of the invention with this method of measurement is at least 220 [U/g moist].

The swellability of the polymer beads in water is expressed by the swelling index [ml moist/ml dry]. The carrier polymer beads of the invention have a swelling index not exceeding 1.5.

Coating of the Carrier Material which can be Used According to the Invention

In the examples, the carrier material is coated at pH 7.5 in potassium phosphate buffer. However, the skilled worker is aware that there is a very large number of other processes ensuring satisfactory coating.

Synthesis of Cephalexin

The precursors (i) 7-aminodeacetoxycephalosporanic acid and (ii) D-phenylglycinamide are employed in concentrations of 10-500 mM, preferably 50-300 mM and particularly preferably of 150-250 mM.

Advantageous Effects of the Invention

The process of the invention makes it possible to synthesize cephalexin with a favorable S/H ratio (synthesis/hydrolysis). It is advantageous in this connection that this is achieved by using a carrier material with particle sizes in the range of 50-500 µm, in particular from 120 to 250 µm. Better technical application properties are achieved in this way, e.g. higher flow rates in fixed bed reactors. The higher flow rates result in better space-time yields. The larger carrier particles also have advantages in batch processes, because they can be filtered off faster. This in turn increases the space-time yield and thus the commercial viability of the process.

EXAMPLES (The following determination method is familiar per se to the person skilled in the area of porous carrier polymer materials and is detailed only for the sake of completeness)

Determination of the binding capacity for penicillin amidase (=penicillin G acylase) from *E. coli* (EC 3.5.1.11).

a) Covalent Bonding of Penicillin Amidase to the Carrier Polymer Material 1 g of carrier polymer material are added to 1530 units of penicillin amidase in 5 ml of sterile 1 M potassium phosphate buffer pH 7.5 and incubated at 23° C. for 48 h.

The polymer beads are then put on a sintered-glass frit (porosity 2 or 3) and washed twice with deionized water and then twice with 0.1 M potassium phosphate buffer pH 7.5, containing 0.05% ethyl 4-hydroxybenzoate, by suction on the frit. The moist weight of the resulting beads loaded with penicillin acylase is determined.

b) Determination of the Binding Capacity 250-300 mg of moist carrier polymer material (polymer beads) coupled to penicillin amidase are put into 20 ml of a 2% strength penicillin G solution in 0.05 M potassium phosphate buffer pH 7.5, containing 0.05% ethyl 4-hydroxybenzoate, at 37° C. Liberated phenylacetic acid is titrated with 0.5 M NaOH while stirring continuously at a constant pH of 7.8 for a period of 10 minutes, recording the NaOH used.

The polymer beads are then obtained as in a) by sucking 20 ml of 0.05 M potassium phosphate buffer pH 7.5, containing 0.05% ethyl 4-hydroxybenzoate, through a glass frit, and the measurement is repeated twice.

c) Calculation of the Binding Capacity

The linear region of the measured curves (normally the region of 1-5 min) is used as basis for the calculation and extrapolated to a 10 min interval. The binding capacity is reported as penicillin amidase units per g of moist carrier polymer material (U/g moist). One unit corresponds to one µmol of hydrolyzed penicillin G per minute (µmol/min); 1 l of 0.5 M NaoH is in this case equivalent to 500 µmol of hydrolyzed penicillin G. (The water content of the carrier polymer material is approximately constant and can therefore be neglected.)

Comparative Example 1

1530 units of penicillin amidase from *E. coli* are dissolved in 6 ml of sterile 1 M potassium phosphate buffer, pH 7.5. The solution is added to 1 g of Eupergit® C (Röhm GmbH & Co. KG, Darmstadt, Germany), and the resulting suspension is incubated at 23° C. for 72 hours. The polymer beads are collected on a sintered glass filter and washed with 0.1 M potassium phosphate buffer. The following cephalexin synthesis and determination of the S/H value follow examples 5 and 6, respectively.

Eupergit® C (a copolymer of N,N'-methylenebismethacrylamide, allyl glycidyl ether and methacrylamide) and processes for its preparation are described in DE-C 27 22 751, U.S. Pat. No. 490,713 and U.S. Pat. No. 4,511,694.

Comparative Example 2

Following WO 97/04086, a cephalexin synthesis is carried out as described in example 6 using the type A enzyme or type B enzyme disclosed therein.

Comparative Example 3

*E. coli* penicillin amidase is immobilized on Sepabeads® FP-EP or Sepabeads® FP-EP/G (Resindion S.R.I., Milan, Italy) as shown in comparative example 1. The following cephalexin synthesis and the determination of the S/H value follow examples 5 and 6, respectively.

Sepabeads® FR-EP or Sepabeads® FP-EP/G is a highly polymeric crosslinked acrylic copolymer having oxirane groups, like Eupergit®. The average particle size according to the manufacturer's information is 150-300 µm.

Comparative Example 4

Measurement of the flow rate of a chromatography column packed with Emphaze™ and the material which can be used according to the invention.
Material: Emphaze Ultralink™ Biosupport Medium, Lot#DC53515, Pierce, average particle size according to the manufacturer's information 50-80 µm;
material which can be used according to the invention, average particle size 208 µm.

Borosilicate glass chromatography columns with bottom glass frits and polypropylene end caps (dimension of the column 1×20 cm) were tested empty for a comparable outflow rate. The carrier materials were suspended in water overnight and then rinsed with water into the particular column, and a packed bed with a height of 6.5 cm was obtained by sedimentation and slow outflow of the liquid. Any voids were removed by gentle tapping. The columns were open at the top and had a constant water column of 23 cm through inflow of water.

The flow rate was achieved only by the hydrostatic pressure. The flow rate was determined using a stopwatch and 10 ml graduated cylinder. The flow rate determined for a preparation which can be used according to the invention was 4.25 ml per minute. The flow rate determined for Emphaze™ was 0.71 ml per minute. The suitability of spherical particles for operating the fixed bed reactors improves as the flow rate increases (higher space-time yield). The pressure drop in fixed bed reactors can also be calculated mathematically: K. Buchholz and B. Gödelmann in "Characterization of immobilized biocatalysts", Dechema Monographs, volume 84, editor K. Buchholz, VCH Weinheim 1979, pages 128-129).

The better technical application properties of the material which can be employed according to the invention for use in fixed bed reactors, compared with Emphaze™, is clearly evident.

Examples 1-3

Consistent Test Conditions in Examples 1-3:
An organic solvent, 3 g of a copolymer of 95 parts of n-butyl methacrylate and 5 parts of 2-trimethyl-ammoniumethyl methacrylate chloride as protective colloid and 5 g of dry ice are introduced into a 2 l stirred flask with thermometer, water trap, reflux condenser, nitrogen-introduction tube. While stirring and passing nitrogen through, a monomer phase consisting of water and methanol in the ratio 1:1.5 (example 1) or of formamide (examples 2 and 3) as diluent, and 10 g of methacrylamide,
    20 g of allyl glycidyl ether,
    20 g of glycidyl methacrylate and
    50 g of methylenebismethacrylamide
and
    2 g of 4,4'-azobis-4-cyanovaleric acid (as polymerization initiator).

is dispersed in the organic phase at 50° C., and then heated to boiling at 65-70° C. The mixture is incubated for about 6 h and then cooled to room temperature. The resulting polymer beads are filtered off with suction, washed and dried in a fluidized bed dryer. The binding capacity for penicillin amidase [U/g moist] and the swelling index is determined [ml moist/ml dry] determined.

The essential test parameters and the results of examples 1-3 are to be found in the following table.

|  | Example 1 (according to the invention | Example 2 (comparative example) | Example 3 (comparative example) |
| --- | --- | --- | --- |
| Organic solvent (continuous phase) | 952 g of cyclohexane | 669 g of cyclohexane | 530 g of n-heptane + 530 g of perchloroethylene |
| Monomers in total | 100 g | 100 g | 100 g |
| Diluent | 80 g of methanol + 120 g of water (=1:1.5) | 263 g of formamide | 264 g of formamide |
| Monomers + diluent (monomer phase) | 300 g | 363 g | 364 g |
| Monomer/diluent ratio | 1:2 | 1:2.63 | 1:2.64 |
| Monomer phase/ continuous phase ratio | 1:3.2 | 1:1.8 | 1:2.9 |
| Binding capacity for penicillin amidase (1530 U) [U/g moist] | 252 | 194 | 192 |
| Swelling index [ml moist/ml dry] | 1.3 | 4.0 | 3.9 |

Example 4

Synthesis of Cephalexin

The reaction is carried out at 25° C. and pH 7.5 in a fixed bed reactor. 10 ml of an aqueous solution of a mixture 0.2 M 7-ADCA and 0.2 M D-phenylglycinamide are passed through a column with 0.5 ml of the immobilized penicillin amidase. During the reaction, the pH is kept constant by adding HCl in an attached stirred reservoir container. Samples are taken and analyzed by HPLC as shown in example 5 at particular time intervals.

Example 5

The products of the reaction from example 4 and of comparative examples 1 to 3 were analyzed by HPLC using an RP-8 column (Merck KGaA, Darmstadt, Germany). The mobile phase used was sterile 67 mM potassium phosphate buffer pH 7.5. Cephalexin was eluted with a 30% strength (volume/volume) aqueous methanol solution.

The cephalexin synthesis rate ($V_{Ceph}$) and the D-phenylglycine hydrolysis rate ($V_{D-PhG}$) was determined from the HPLC analysis, and the S/H value (synthesis rate/hydrolysis rate ($V_{Ceph}/V_{D-PhG}$) ratio was calculated therefrom. The results are shown in the following table:

| Enzyme source | Carrier/immobilizates | $V_{Ceph}/V_{D-PhG}$ |
| --- | --- | --- |
| E. coli | according to the invention | 4.6 |
| E. coli | Type A from WO 97/04086 (see comparative example 2) | 3.3 |
| E. coli | Type B from WO 97/04086 (see comparative example 2) | 3.3 |
| E. coli | Comparative example 1 | 3.5 |
| E. coli | Comparative example 3 (Sepabeads FP-EP) | 3.2 |
| E. coli | Comparative example 3 (Sepabeads FP-EP/G) | 2.9 |

The value for the process of the invention is composed of 7 test series carried out in parallel, which resulted in the following S/H values: 5.3, 4.7, 3.6, 4.6, 4.3, 5.2, 4.7;

The significant improvement of about 30% in the S/H value which can be achieved with the process of the invention compared with the comparative examples is clearly evident.

The invention claimed is:

1. A process for the preparation of cephalexin, comprising:
    contacting an aqueous solution, comprising:
    (i) 7-aminodeacetoxycephalosporanic acid, and
    (ii) D-phenylglycinamide,
    in a ratio from 1:2 to 2:1, with a coated carrier,
    wherein the carrier comprises crosslinked hydrophilic carrier polymer materials which are able to form covalent bonds in a polymer-analogous reaction with nucleophilic groups of ligands, are in bead form and can be prepared by inverse bead polymerization of a monomer phase which consists of monomers and a diluent,
    wherein the monomers are:
        (a) 5-40% by weight of hydrophilic monomers which are capable of free-radical polymerization, have a vinyl group and form at least 10% strength aqueous solutions at room temperature,
        (b) 30-50% by weight of monomers which are capable of free-radical polymerization and have a vinyl group and an additional functional group which is able to enter into covalent bonds in a polymer-analogous reaction with the nucleophilic groups of the ligands,
        (c) 20-60% by weight of crosslinking monomers which are capable of free-radical polymerization and have two or more ethylenically unsaturated polymerizable groups, and
    with the proviso that a), b) and c) add up to 100% by weight, and
    wherein the diluent is a mixture of methanol and water in the ratio from 1:1.0 to 1:4.0, and
    wherein the monomer phase is dispersed to droplets in a continuous phase comprising an organic solvent comprising an aliphatic hydrocarbon having 5-7 carbon atoms, and where the ratio of monomer phase to continuous phase is from 1:2.0 to 1:4.0, and in this form undergo free-radical polymerization in the presence of a polymerization initiator and of a protective colloid, with the proviso that the ratio of the monomers to the diluent is from 1:1.7 to 1:2.4, and
    wherein the carrier polymer materials are coated with penicillin amidase to form the coated carrier.

2. The process as claimed in claim 1, wherein the monomers are:
    a) acrylamide and/or methacrylamide
    b) glycidyl methacrylate and/or allyl glycidyl ether
    c) N,N'-methylenebisacrylamide or N,N'-methylene-bis-methacrylamide.

3. The process as claimed in claim 1, wherein the organic solvent is cyclohexane.

4. The process as claimed in claim 1, wherein the penicillin amidase is derived from *E. coli*.

5. A process for the synthesis of cephalexin, comprising:
    contacting the reactants for cephalexin with a carrier material,
    wherein the carrier material comprises crosslinked hydrophilic carrier polymer materials which are able to form covalent bonds in a polymer-analogous reaction with nucleophilic groups of ligands, are in bead form and can be prepared by inverse bead polymerization of a monomer phase which consists of monomers and a diluent, wherein the monomers are:
- (a) 5-40% by weight of hydrophilic monomers which are capable of free-radical polymerization, have a vinyl group and form at least 10% strength aqueous solutions at room temperature,
- (b) 30-50% by weight of monomers which are capable of free-radical polymerization and have a vinyl group and an additional functional group which is able to enter into covalent bonds in a polymer-analogous reaction with the nucleophilic groups of the ligands,
- (c) 20-60% by weight of crosslinking monomers which are capable of free-radical polymerization and have two or more ethylenically unsaturated polymerizable groups, and with the proviso that a), b) and c) add up to 100% by weight, and wherein the diluent is a mixture of methanol and water in the ratio from 1:1.0 to 1:4.0, and wherein the monomer phase is dispersed to droplets in a continuous phase comprising an organic solvent comprising an aliphatic hydrocarbon having 5-7 carbon atoms, and where the ratio of monomer phase to continuous phase is from 1:2.0 to 1:4.0, and in this form undergo free-radical polymerization in the presence of a polymerization initiator and of a protective colloid, with the proviso that the ratio of the monomers to the diluent is from 1:1.7 to 1:2.4.

6. The process as claimed in claim 1, wherein the monomers a) are methacrylamide.

7. The process as claimed in claim 1, wherein the monomers b) are glycidyl methacrylate and allyl glycidyl ether.

8. The process as claimed in claim 1, wherein the monomers c) are N,N'-methylene-bismethacrylamide.

9. The process as claimed in claim 1, wherein the carrier polymer material has a size of from 50 to 500 µm.

10. The process as claimed in claim 1, wherein the carrier polymer material has a size of from 120 to 250 µm.

11. The process as claimed in claim 5, wherein the monomers a) are methacrylamide.

12. The process as claimed in claim 5, wherein the monomers b) are glycidyl methacrylate and allyl glycidyl ether.

13. The process as claimed in claim 5, wherein the monomers c) are N,N'-methylene-bismethacrylamide.

14. The process as claimed in claim 5, wherein the carrier polymer material has a size of from 50 to 500 µm.

15. The process as claimed in claim 5, wherein the carrier polymer material has a size of from 120 to 250 µm.

* * * * *